US010258565B2

(12) United States Patent
Seward et al.

(10) Patent No.: US 10,258,565 B2
(45) Date of Patent: *Apr. 16, 2019

(54) INTRAVASCULAR DELIVERY OF NANOPARTICLE COMPOSITIONS AND USES THEREOF

(71) Applicants: Mercator MedSystems, Inc., San Leandro, CA (US); Abraxis BioScience, LLC, Summit, NJ (US)

(72) Inventors: Kirk Seward, San Francisco, CA (US); Neil P. Desai, Pacific Palisades, CA (US)

(73) Assignees: ABRAXIS BIOSCIENCE, LLC, Summit, NJ (US); MERCATOR MEDSYSTEMS, INC., San Leandro, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/851,478

(22) Filed: Dec. 21, 2017

(65) Prior Publication Data

US 2018/0147139 A1 May 31, 2018

Related U.S. Application Data

(63) Continuation of application No. 14/714,131, filed on May 15, 2015, now Pat. No. 9,884,013, which is a continuation of application No. 14/113,568, filed as application No. PCT/US2012/035626 on Apr. 27, 2012, now Pat. No. 9,061,014.

(60) Provisional application No. 61/557,851, filed on Nov. 9, 2011, provisional application No. 61/518,084, filed on Apr. 28, 2011.

(51) Int. Cl.
| | |
|---|---|
| A61K 9/00 | (2006.01) |
| A61K 31/436 | (2006.01) |
| A61K 38/38 | (2006.01) |
| A61M 25/00 | (2006.01) |
| A61M 25/10 | (2013.01) |
| A61K 47/64 | (2017.01) |
| A61K 47/69 | (2017.01) |

(52) U.S. Cl.
CPC .......... *A61K 9/0019* (2013.01); *A61K 31/436* (2013.01); *A61K 38/38* (2013.01); *A61K 38/385* (2013.01); *A61K 47/643* (2017.08); *A61K 47/6921* (2017.08); *A61K 47/6931* (2017.08); *A61M 25/0084* (2013.01); *A61M 25/104* (2013.01); *A61M 2025/0089* (2013.01)

(58) Field of Classification Search
CPC .............................. A61K 9/0019; A61K 47/643
USPC ....................................................... 514/291
See application file for complete search history.

(56) References Cited

U.S. PATENT DOCUMENTS

| | | |
|---|---|---|
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,916,596 A | 6/1999 | Desai et al. |
| 5,997,904 A | 12/1999 | Magdassi et al. |
| 6,096,331 A | 8/2000 | Desai et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,547,303 B1 | 3/2003 | Anderson |
| 6,565,842 B1 | 5/2003 | Desai et al. |
| 6,652,884 B2 | 11/2003 | Falciani |
| 6,720,350 B2 | 4/2004 | Kunz et al. |
| 6,749,868 B1 | 6/2004 | Desai et al. |
| 6,753,006 B1 | 6/2004 | Desai et al. |
| 6,860,867 B2 | 3/2005 | Seward et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,728,528 B2 | 5/2014 | Biggs |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |

(Continued)

FOREIGN PATENT DOCUMENTS

| | | |
|---|---|---|
| CN | 1839806 A | 10/2006 |
| CN | 101160123 A | 4/2008 |

(Continued)

OTHER PUBLICATIONS

US 8,968,752 B2, 03/2015, Desai et al. (withdrawn)

(Continued)

*Primary Examiner* — Savitha M Rao
*Assistant Examiner* — Taina D Matos Negron
(74) *Attorney, Agent, or Firm* — Morrison & Foerster LLP

(57) ABSTRACT

The present invention provides methods of delivering a composition comprising nanoparticles that comprise a macrolide and an albumin by directly injecting the nanoparticle composition into the blood vessel wall or the tissue surrounding the blood vessel wall. The methods can be used for inhibiting negative remodeling or vascular fibrosis in the blood vessel and are useful for treating various diseases.

21 Claims, 10 Drawing Sheets

(56) References Cited

U.S. PATENT DOCUMENTS

| | | |
|---|---|---|
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,308,180 B2 | 4/2016 | De et al. |
| 9,370,494 B2 | 6/2016 | Yeo et al. |
| 9,393,318 B2 | 7/2016 | Desai et al. |
| 9,399,071 B2 | 7/2016 | Desai et al. |
| 9,399,072 B2 | 7/2016 | Desai et al. |
| 9,446,003 B2 | 9/2016 | Desai et al. |
| 9,511,046 B2 | 12/2016 | Desai et al. |
| 9,561,288 B2 | 2/2017 | Desai et al. |
| 9,585,960 B2 | 3/2017 | Foss et al. |
| 9,597,409 B2 | 3/2017 | Desai et al. |
| 9,675,578 B2 | 6/2017 | Desai et al. |
| 9,724,323 B2 | 8/2017 | Desai et al. |
| 9,884,013 B2 | 2/2018 | Seward et al. |
| 9,962,373 B2 | 5/2018 | Desai et al. |
| 10,076,501 B2 | 9/2018 | Foss et al. |
| 2006/0189941 A1 | 8/2006 | Seward et al. |
| 2006/0263434 A1 | 11/2006 | Desai et al. |
| 2007/0082838 A1 | 4/2007 | De Tapas et al. |
| 2007/0106257 A1 | 5/2007 | Seward et al. |
| 2008/0145439 A1 | 6/2008 | Lobl et al. |
| 2008/0181927 A1 | 7/2008 | Zhao |
| 2008/0286372 A1 | 11/2008 | Pacetti et al. |
| 2009/0142306 A1 | 6/2009 | Seward et al. |
| 2009/0204104 A1 | 8/2009 | Tremble et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0305546 A1 | 12/2010 | Seward et al. |
| 2011/0118342 A1 | 5/2011 | De et al. |
| 2011/0151012 A1 | 6/2011 | Desai et al. |
| 2011/0190876 A1 | 8/2011 | Zhao |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai et al. |
| 2016/0015681 A1 | 1/2016 | Desai et al. |
| 2016/0015817 A1 | 1/2016 | Benettaib et al. |
| 2016/0151325 A1 | 6/2016 | Desai et al. |
| 2016/0228401 A1 | 8/2016 | Desai et al. |
| 2016/0374952 A1 | 12/2016 | Yeo et al. |
| 2017/0007569 A1 | 1/2017 | De et al. |
| 2017/0014373 A1 | 1/2017 | Desai et al. |
| 2017/0020824 A1 | 1/2017 | Desai et al. |
| 2017/0049711 A1 | 2/2017 | Desai et al. |
| 2017/0100344 A1 | 4/2017 | Desai et al. |
| 2017/0105951 A1 | 4/2017 | Desai et al. |
| 2017/0157035 A1 | 6/2017 | Seward et al. |
| 2017/0172975 A1 | 6/2017 | Desai et al. |
| 2017/0181988 A1 | 6/2017 | Desai et al. |
| 2017/0202782 A1 | 7/2017 | Pierce et al. |
| 2017/0224627 A1 | 8/2017 | Foss et al. |
| 2017/0333384 A1 | 11/2017 | Desai et al. |
| 2017/0340599 A1 | 11/2017 | Desai et al. |
| 2018/0015181 A1 | 1/2018 | Desai et al. |
| 2018/0064679 A1 | 3/2018 | Pierce et al. |
| 2018/0133157 A1 | 5/2018 | Desai et al. |
| 2018/0153820 A1 | 6/2018 | Desai et al. |
| 2018/0153863 A1 | 6/2018 | Desai et al. |
| 2018/0169017 A1 | 6/2018 | Desai et al. |
| 2018/0177770 A1 | 6/2018 | Desai et al. |
| 2018/0177771 A1 | 6/2018 | Desai et al. |
| 2018/0214425 A1 | 8/2018 | Desai et al. |
| 2018/0256551 A1 | 9/2018 | Desai et al. |

FOREIGN PATENT DOCUMENTS

| | | |
|---|---|---|
| CN | 101257861 A | 9/2008 |
| CN | 101442991 A | 5/2009 |
| CN | 101549187 A | 10/2009 |
| CN | 101730526 A | 6/2010 |
| EP | 2 108 390 A2 | 10/2009 |
| JP | 2004-523537 A | 8/2004 |
| JP | 2005-525411 A | 8/2005 |
| JP | 2008-530248 A | 8/2008 |
| JP | 2008-540659 A | 11/2008 |
| JP | 2010-520289 A | 6/2010 |
| WO | WO-02/06335 A2 | 8/2002 |
| WO | WO-02/06335 A3 | 8/2002 |
| WO | WO-2003/092741 A1 | 11/2003 |
| WO | WO-2006/068877 A2 | 6/2006 |
| WO | WO-2006/089290 A1 | 8/2006 |
| WO | WO-2006/124739 A1 | 11/2006 |
| WO | WO-2007/001744 A2 | 1/2007 |
| WO | WO-2007/001744 A3 | 1/2007 |
| WO | WO-2008/060651 A2 | 5/2008 |
| WO | WO-08/137148 A2 | 11/2008 |
| WO | WO-08/137148 A3 | 11/2008 |
| WO | WO-2008/144137 A1 | 11/2008 |
| WO | WO-2008/109163 A1 | 12/2008 |
| WO | WO-2011/137114 A1 | 11/2011 |

OTHER PUBLICATIONS

Altmayer, P. et al. (1995). "Propofol Binding to Human Blood Proteins," *Arzneimittel Forschung Drug Research* 45(II)(10):1053-1056.

Carter, D.C. et al. (1994). Structure of Serum Albumin, *Adv. Protein Chem.* 45:153-203.

(56) References Cited

OTHER PUBLICATIONS

Curry, S. et al. (Sep. 1998). Crystal Structure of Human Serum Albumin Complexed With Fatty Acid Reveals an Asymmetric Distribution of Binding Sites, *Nat. Struct. Biol.* 5(9):827-835.

Fehske, K.J. et al. (1981) "The Location of Drug Binding Sites in Human Serum Albumin," *Biochem. Pharamcol.* 30(7):687-692.

Finlayson, J.S. (1980). Albumin Products, *Seminars in Thrombosis and Hemostatsis* 6(2):85-120.

Garrido, M.J. et al. (Nov.-Dec. 1994). "Binding Characteristics of Propofol to Plasma Proteins and Possible Interactions," *Rev. Esp. Anestesiol. Reanim.* 41(6):308-312. (English Summary).

Gasper, W.J. et al. (Jun. 1, 2011). "Peri-Adventitial Delivery of a Nanoparticle Albumin-Bound Rapamycin Reduces Luminal Stenosis in a Porcine Femoral Artery Balloon Injury Model," Abstract No. PS212, *Journal of Vascular Surgery* 53(17S):84S-85S.

Gertz, Z.M. et al. (2011). "Local Drug Delivery for Treatment of Coronary and Peripheral Artery Disease," *Cardiovascular Therapeutics* 29:e54-e66.

Goel, S.A. et al. (2012, e-pub. Aug. 22, 2012). "Mechanisms of Post-Intervention Arterial Remodelling," *Cardiovascular Research* 96:363-371.

He, X. et al. (Jul. 16, 1992). "Atomic Structure and Chemistry of Human Serum Albumin," *Nature* 358:209-215.

Hauser, C.J. et al. (Jun. 1980). "Oxygen Transport Responses to Colloids and Crystalloids in Critically Ill Surgical Patients," Surgery, Gynecology and Obstetrics 150(6):811-816.

Kragh-Hansen, U. (Feb. 1990). "Structure and Ligand Binding Properties of Human Serum Albumin," *Dan. Med. Bull.* 37(1)57-84.

Müller, B.G. et al. (1996). "Albumin Nanospheres as Carriers for Passive Drug Targeting: An Optimized Manufacturing Technique," *Pharmaceutical Research* 13(1):32-37.

Paál, K. et al.(2001). "High Affinity Binding of Paclitaxel to Human Serum Albumin," *Eur. J. Biochem.* 268(7):2187-2191.

Ponticos, M. et al. (2014). "Extracellular Matrix Synthesis in Vascular Disease: Hypertension, and Atherosclerosis," *Journal of Biomedical Research* 28(1):25-39.

Purcell, M. et al. (2000). "Interaction of Taxol with Human Serum Albumin," *Biochim. Biophys. Acat* 1478(a):61-68.

Rajathurai, T. et al. (Apr. 1, 2010). "Periadventitial Rapamycin-Eluting Microbeads Promote Vein Graft Disease in Long-Term Pig Vein-Into-Artery Interposition Grafts," *Circ. Cardiovas. Interv.* 3(2):157-165.

Sugio, S. et al. (1999). "Crystal Structure of Human Serum Albumin at 2.5 Å Resolution," *Protein Eng.* 12(6):439-446.

Tullis, J.L. (Jan. 24, 1977). "Albumin. 1. Background and Use," *JAMA* 237(4):355-360.

Tullis, J.L. (Jan. 31, 1977). "Albumin. 2. Guidelines for Clincial use," *JAMA* 237(5):460-463.

Urien, S. et al. (1996). "Docetaxel Serum Protein Binding With High Affinity to $Alpha_1$-Acid Glycoprotein," *Invest. New Drugs* 14:147-151.

Vorum, H. (Nov. 1999). "Reversible Ligand Binding to Human Serum Albumin," *Danish Medical Bulletin* 46(5):379-399.

International Search Report dated Jul. 30, 2012, for PCT Patent Application No. PCT/US2012/035626, filed on Apr. 27, 2012, 5 pages.

Written Opinion dated Jul. 30, 2012, for PCT Patent Application No. PCT/US2012/035626, filed on Apr. 27, 2012, 7 pages.

European Examination Communication pursuant to Article 94(3) EPC, dated Sep. 19, 2017, for European Application No. 12777153.3, Filed on Nov. 13, 2013, 6 Pages.

European Examination Communication pursuant to Article 94(3) EPC, dated Jun. 4, 2018, for European Application No. 12777153.3, filed on Nov. 13, 2013, 6 pages.

U.S. Appl. No. 15/399,366, filed Jan. 5, 2017, for Pierce et al. (Copy not submitted herewith pursuant to the waiver of 37 C.F.R. § 1.98(a)(2)(iii) issued by the Office on Sep. 21, 2004).

U.S. Appl. No. 15/462,361, filed Mar. 17, 2017, for Tao et al. (Copy not submitted herewith pursuant to the waiver of 37 C.F.R. § 1.98(a)(2)(iii) issued by the Office on Sep. 21, 2004).

U.S. Appl. No. 15/663,351, filed Jul. 28, 2017, for Desai et al. (Copy not submitted herewith pursuant to the waiver of 37 C.F.R. § 1.98(a)(2)(iii) issued by the Office on Sep. 21, 2004).

U.S. Appl. No. 15/796,578, filed Oct. 27, 2017, for Desai et al. (Copy not submitted herewith pursuant to the waiver of 37 C.F.R. § 1.98(a)(2)(iii) issued by the Office on Sep. 21, 2004).

U.S. Appl. No. 15/879,320, filed Jan. 24, 2018, for Desai et al. (Copy not submitted herewith pursuant to the waiver of 37 C.F.R. § 1.98(a)(2)(iii) issued by the Office on Sep. 21, 2004).

U.S. Appl. No. 15/981,276, filed May 16, 2018, for Desai et al. (Copy not submitted herewith pursuant to the waiver of 37 C.F.R. § 1.98(a)(2)(iii) issued by the Office on Sep. 21, 2004).

U.S. Appl. No. 16/101,027, filed Aug. 10, 2018, for Desai et al. (Copy not submitted herewith pursuant to the waiver of 37 C.F.R. § 1.98(a)(2)(iii) issued by the Office on Sep. 21, 2004).

U.S. Appl. No. 16/107,419, filed Aug. 21, 2018, for Foss et al. (Copy not submitted herewith pursuant to the waiver of 37 C.F.R. § 1.98(a)(2)(iii) issued by the Office on Sep. 21, 2004).

U.S. Appl. No. 16/140,339, filed Sep. 24, 2018, for Desai et al. (Copy not submitted herewith pursuant to the waiver of 37 C.F.R. § 1.98(a)(2)(iii) issued by the Office on Sep. 21, 2004).

INTRAVASCULAR DELIVERY OF NANOPARTICLE COMPOSITIONS AND USES THEREOF

RELATED APPLICATIONS

This application is a continuation of U.S. patent application Ser. No. 14/714,131, filed May 15, 2015, which is a continuation of U.S. patent application Ser. No. 14/113,568 (U.S. Pat. No. 9,061,014), which adopts the international filing date of Apr. 27, 2012, which is a National Phase application under 35 U.S.C. § 371 of International Application No. PCT/US12/35626, filed Apr. 27, 2012, which claims priority benefit of U.S. Provisional Application Ser. No. 61/518,084, filed Apr. 28, 2011 and U.S. Provisional Application Ser. No. 61/557,851, filed Nov. 9, 2011, the contents of each are hereby incorporated herein by reference in their entirety.

TECHNICAL FIELD

The present invention relates to methods of delivering and use of a composition comprising nanoparticles that comprise a macrolide and an albumin by directly injecting the nanoparticle composition into the blood vessel wall or the tissue surrounding the blood vessel wall.

BACKGROUND

Coronary artery disease is one of the leading causes of death throughout the world. While coronary artery bypass surgery is an effective treatment for stenosed arteries resulting from atherosclerosis and other causes, it is a highly invasive procedure and requires substantial hospital and recovery time. Percutaneous transluminal coronary angioplasty (PTCA), commonly referred to as balloon angioplasty, is less invasive, less traumatic, and significantly less expensive than bypass surgery. The effectiveness of balloon angioplasty has improved significantly with the introduction of stenting which involves the placement of a scaffold structure within the artery which has been treated by balloon angioplasty. The stent inhibits abrupt reclosure of the artery and has some benefit in reducing subsequent restenosis resulting from hyperplasia. Despite such improvement, patients who have undergone angioplasty procedures with subsequent stenting still suffer from a high incidence of restenosis resulting from hyperplasia. Implanting of stents which have been coated with anti-proliferative drugs can significantly reduce the occurrence of hyperplasia.

Albumin-based nanoparticle compositions have been developed as a drug delivery system for delivering substantially water insoluble drugs such as a taxanes. See, for example, U.S. Pat. Nos. 5,916,596; 6,506,405; 6,749,868; and 6,537,579, 7,820,788, and 7,923,536. It is generally believed that the albumin-based nanoparticle, such as Abraxane®, when introduced into the blood stream, would dissolve into albumin-drug complexes. Such complexes utilize the natural properties of the protein albumin to transport and deliver substantially water insoluble drugs to the site of disease, such as tumor sites. In addition, the albumin-based nanoparticle technology offers the ability to improve a drug's solubility by avoiding the need for toxic chemicals, such as solvents, in the administration process, thus potentially improving safety through the elimination of solvent-related side effects.

The disclosures of all publications, patents, patent applications and published patent applications referred to herein are hereby incorporated herein by reference in their entirety.

BRIEF SUMMARY OF THE INVENTION

The present application in some embodiment provides a method of delivering a composition comprising nanoparticles comprising albumin and a macrolide to a blood vessel, wherein the method comprises injecting into the blood vessel wall or tissue surrounding the blood vessel wall an effective amount of a composition comprising nanoparticles comprising a macrolide and an albumin. In some embodiments, there is provided a method of inhibiting negative remodeling in a blood vessel in an individual in need thereof, comprising injecting into the blood vessel wall or tissue surrounding the blood vessel wall an effective amount of a composition comprising nanoparticles comprising a macrolide and an albumin. In some embodiments, there is provided a method of inhibiting vascular fibrosis (such as medial fibrosis or adventitia fibrosis) in a blood vessel in an individual in need thereof, comprising injecting into the blood vessel wall or tissue surrounding the blood vessel wall an effective amount of a composition comprising nanoparticles comprising a macrolide and an albumin. In some embodiments, there is provided a method of reducing proliferation index in a blood vessel in an individual in need thereof, comprising injecting into the blood vessel wall or tissue surrounding the blood vessel wall an effective amount of a composition comprising nanoparticles comprising a macrolide and an albumin. In some embodiments, there is provided a method of promoting positive remodeling in a blood vessel in an individual in need thereof, comprising injecting into the blood vessel wall or tissue surrounding the blood vessel wall an effective amount of a composition comprising nanoparticles comprising a macrolide and an albumin.

In some embodiments, the blood vessel is an artery, such as a coronary artery or a peripheral artery. In some embodiments, the artery is selected from the group consisting of renal artery, cerebral artery, pulmonary artery, and artery in the leg. In some embodiments, the blood vessel is a vein.

In some embodiments, the nanoparticle composition is injected into the blood vessel wall. In some embodiments, the nanoparticle composition is injected into the tissue surrounding the blood vessel wall. In some embodiments, the nanoparticle composition is injected into the adventitial tissue of the blood vessel.

In some embodiments, the nanoparticle composition is injected at a dose of about 0.001 mg to about 100 mg, including for example about 0.05 mg to about 5 mg. In some embodiments, the injection volume of the nanoparticle composition is about 0.01 ml to about 50 ml, including for example, about 0.5 ml to about 5 ml. In some embodiments, the nanoparticle composition is injected though a catheter with a needle, such as a deployable needle. In some embodiments, the nanoparticle composition is injected at least once a year. In some embodiments, the nanoparticle composition is injected only once.

In some embodiments, the nanoparticle composition is injected distal to the disease site. In some embodiments, the nanoparticle composition is injected proximal to the disease site. In some embodiments, the nanoparticle composition is injected at or adjacent to the disease site. In some embodiments, the nanoparticle composition is injected remotely from the disease site. In some embodiments, the nanoparticle composition is injected at least about 2 cm (including for example at least any of 3, 4, 5, 6, 7, 8, 9, or 10 cm) away from the disease site.

In some embodiment according to any of the above embodiments, the individual has any one of: angina, myocardial infarction, congestive heart failure, cardiac arrhythmia, peripheral artery disease, claudication, or chronic limb ischemia. In some embodiments, the individual is a human. In some embodiments, the method is carried out during vascular interventional procedure, including but not limited to, angioplasty (such as percutaneous translumenal coronary angioplasty), stenting, or atherectomy. In some embodiments, the method is carried out after a vascular interventional procedure, including but not limited to, angioplasty, stenting, or atherectomy.

In some embodiments according to any of the above embodiments, the macrolide is rapamycin or a derivative thereof. In some embodiments, the macrolide is rapamycin. In some embodiments according to any of the above embodiments, the nanoparticles in the composition have an average diameter of no greater than about 200 nm, such as no greater than about 100 nm. In some embodiments, the nanoparticles in the composition have an average diameter of no less than about 70 nm. In some embodiments, the macrolide in the nanoparticles is coated with albumin.

Also provided are kits and devices for use in any of the methods described herein. For example, in some embodiments, there is provided a catheter with a needle (such as a deployable needle), wherein the needle contains a composition comprising nanoparticles comprising a macrolide and an albumin. In some embodiments, the macrolide is rapamycin. In some embodiments, the nanoparticles comprise a macrolide coated with albumin. In some embodiments, the nanoparticles in the composition have an average diameter of no greater than about 200 nm, such as no greater than about 100 nm. In some embodiments, the nanoparticles in the composition have an average diameter of no less than about 70 nm.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 1A shows a deflated balloon which sheathes the needle. FIG. 1B shows an inflated balloon with the needle extruding outward.

FIG. 2A shows a flow chart for pharmacokinetics studies. FIG. 2B shows a flow chart for histopathology studies.

FIGS. 6A and 6C show staining with H&E. FIGS. 6B and 6D show staining with trichrome.

DETAILED DESCRIPTION OF THE INVENTION

Figure 1A:
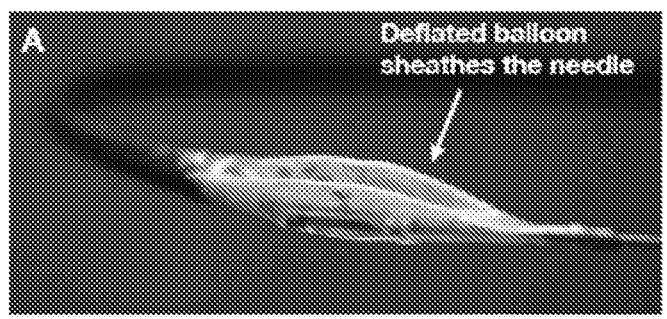
FIGS. 1A and 1B provide images of the micro-infusion catheter utilized for periadventitial injection of Nab-rapamycin in the femoral artery.

The present application provides methods of delivering a composition comprising nanoparticles comprising a macrolide and an albumin (the "nanoparticle composition") to a blood vessel, wherein the method comprises injecting into the blood vessel wall or tissue surrounding the blood vessel wall an effective amount of a composition comprising nanoparticles comprising a macrolide and an albumin. Such method can be useful, for example, for inhibiting negative remodeling in the blood vessel and/or inhibiting vascular fibrosis in the blood vessel, and are thus useful for treating various diseases associated with negative remodeling and/or vascular fibrosis.

Using a porcine femoral artery balloon injury model, it was shown that a nanoparticle composition comprising a macrolide and an albumin, namely, Nanoparticle Albumin-Bound (Nab) Rapamycin (Nab-Rapamycin), when injected into the periadventitial tissue of a blood vessel, significantly decreased negative remodeling of the balloon-injured blood vessel and medial fibrosis in the blood vessel. Within one hour after the injection, the rapamycin level in the perivascular tissue was about 1500 times higher than that in the blood within an hour, and rapamycin was retained in the perivascular tissue for at least 8 days. Periadventitial injection of a nanoparticle composition therefore can be an effective method for inhibiting negative remodeling, inhibiting vascular fibrosis, as well as for treating various diseases associated with negative remodeling and/or vascular fibrosis.

Thus, the present application in one aspect provides a method of inhibiting negative remodeling or vascular fibrosis in the blood vessel of an individual in need thereof, comprising injecting into the blood vessel wall or tissue surrounding the blood vessel wall an effective amount of a composition comprising nanoparticles comprising a macrolide and an albumin.

In another aspect, there is provided a method of delivering a composition comprising nanoparticles comprising a macrolide and an albumin to a blood vessel, wherein the method comprises injecting into the blood vessel wall or tissue surrounding the blood vessel wall an effective amount of a composition comprising nanoparticles comprising a macrolide and an albumin.

Further provided are kits and devices (such as a catheter with a needle) that are useful for the methods described herein.

Definitions

The term "individual" refers to a mammal and includes, but is not limited to, human, bovine, horse, feline, canine, rodent, or primate.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Methods of the Present Invention

The present application in some embodiments provides a method of delivering a composition comprising nanoparticles comprising albumin and a macrolide (such as rapamycin or a derivative thereof, for example rapamycin) to a blood vessel, wherein the method comprises injecting into the blood vessel wall or tissue surrounding the blood vessel wall an effective amount of a composition comprising nanoparticles comprising a macrolide and an albumin. In some embodiments, there is provided a method of delivering a composition comprising nanoparticles comprising albumin and a macrolide (such as rapamycin) to a blood vessel, wherein the method comprises injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of delivering a composition comprising nanoparticles comprising albumin and a macrolide (such as rapamycin) to a blood vessel, wherein the method comprises injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of delivering a composition comprising nanoparticles comprising albumin and a macrolide (such as rapamycin) to a blood vessel, wherein the method comprises injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of delivering Nab-rapamycin to a blood vessel, wherein the method comprises injecting into the blood vessel wall or tissue surrounding the blood vessel wall an effective amount of Nab-rapamycin. In some embodiments, the nanoparticle composition is injected at or adjacent to a disease site (or lesion site), such as no more than about 2, 1, or 0.5 cm away from the disease site (or lesion site). In some embodiments, the nanoparticle composition is injected remotely from a disease site (such example at least about any of 1, 2, 3, 4, 5, 6, 7, 8, 9, or 10 cm away from the disease site).

A typical blood vessel wall has an endothelium which is the layer of the wall which is exposed to the blood vessel lumen. Underlying the endothelium is the basement membrane which in turn is surrounded by the intima. The intima, in turn, is surrounded by the internal elastic lamina over which is located the media. In turn, the media is covered by the external elastic lamina which acts as the outer barrier separating the blood vessel wall from the adventitial tissue, which surrounds the blood vessel wall. The methods described herein include injection of the nanoparticle composition into any one of these layers of the blood vessel wall. In some embodiments, the nanoparticle composition is injected into the endothelium. In some embodiments, the nanoparticle composition is injected into the basement membrane. In some embodiments, the nanoparticle composition is injected into the intima. In some embodiments, the nanoparticle composition is injected into the internal elastic lamina. In some embodiments, the nanoparticle is injected into the media. In some embodiments, the nanoparticle is injected into the external elastic lamina. In some embodiments, the nanoparticle composition is injected into any one of the following regions of a blood vessel: tunica intima (contains endothelium, basement membrane, internal elastic lamina), tunica media (contains smooth muscle cells), and tunica adventitia (contains external elastic membrane, collagen fibres).

"Tissue surrounding the blood vessel wall," used herein interchangeably with the terms "perivascular" or "periadventitial," refers to the region over the outer surface of the blood vessel wall. This includes the adventitial tissue of the blood vessel, as well as regions beyond the adventitial tissue. By controlling the site of the injection of the nanoparticle compositions, the nanoparticle composition can be injected to the specific desired locations.

Methods and devices have been developed for the purpose of injecting therapeutic agents into the blood vessel wall and tissues surrounding the blood vessel wall. For example, catheters carrying needles capable of delivering therapeutic and other agents deep into the adventitial layer surrounding blood vessel lumens have been described in U.S. Pat. Nos. 6,547,303, 6,860,867 and U.S. Patent Application Publication Nos. 2007/0106257, 2010/0305546, and 2009/0142306, the content of each of these are specifically incorporated herein by reference in their entirety. The methods of the present invention in some embodiments use a catheter having a needle for the injection of the nanoparticle composition. In some embodiments, the needle is deployable. The catheter can be advanced intravascularly to a target injection site (which may or may not be a disease region) in a blood vessel. The needle in the catheter is advanced through the blood vessel wall so that an aperture on the needle is positioned in the desired region (for example the perivascular region), and the nanoparticle compositions can be injected through the aperture of the needled into the desired region.

For example, in some embodiments there is provided a method of delivering a composition comprising nanoparticles comprising albumin and a macrolide (such as rapamycin or derivative thereof, for example rapamycin) to a blood vessel, wherein the method comprises injecting (for example via a catheter with a needle) into the tissue surrounding the blood vessel wall an effective amount of a composition comprising nanoparticles comprising a macrolide and an albumin. In some embodiments, there is provided a method of delivering a composition comprising nanoparticles comprising albumin and a macrolide (such as rapamycin) to a blood vessel, wherein the method comprises injecting (for example via a catheter with a needle) into the tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of delivering a composition comprising nanoparticles comprising albumin and a macrolide (such as rapamycin) to a blood vessel, wherein the method comprises injecting (for example via a catheter with a needle) into the tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of delivering a composition comprising nanoparticles comprising albumin and a macrolide (such as rapamycin) to a blood vessel, wherein the method comprises injecting (for example via a catheter with a needle) into the tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of delivering Nab-rapamycin to a blood vessel, wherein the method comprises injecting (for example via a catheter with a needle) into the tissue surrounding the blood vessel wall an effective amount of Nab-rapamycin. In some embodiments, the nanoparticle composition is injected at a disease site. In some embodiments, the nanoparticle composition is injected distal to a disease site (such example at least about any of 1, 2, 3, 4, 5, 6, 7, 8, 9, or 10 cm away from the disease site).

In some embodiments, the nanoparticle composition is injected into the adventitial tissue of the blood vessel. The adventitial tissue is the tissue surrounding the blood vessel, for example the tissue beyond the external elastic lamina of an artery or beyond the tunica media of a vein. The adventitia has a high concentration of lipid. In some embodiments, the nanoparticle composition is injected into the vasa vasorum region of the adventitia. In some embodiments, the nanoparticle composition, upon injection, can disperse through the adventitia circumferentially, longitudinally, and/or transmurally from the injection site with respect to the axis of the blood vessel from which the nanoparticle composition is being injected (herein after referred to as "volumetric distribution"). In some embodiments, the drug (in an albumin-bound form or in nanoparticle form) distributes over a distance of at least about 1 cm (for example at least about any of 2 cm, 3 cm, 4 cm, 5 cm, 6 cm, 7 cm, or more) longitudinally and/or at least 1 cm (for example at least about any of 2 cm, 3 cm, 4 cm, 5 cm, 6 cm, 7 cm, or more) radially from the site of injection over a time period no greater than 60 minutes. In some embodiments, a concentration of a drug measured at all locations at least 2 cm from the delivery site is at least 10% (such as at least about any of 20%, 30%, 40%, or 50%) of the concentration at the delivery site, for example after a period of 60 minutes. In some embodiments, the drug (in an albumin-bound form or in nanoparticle form) distributes transmurally throughout the endothelial and intimal layers of the blood vessel, the media, and the muscular layer. While periadventitial administration of pharmaceutical agents has previously been reported to allow volumetric distribution of a pharmaceutical agent, it was believed larger substances are not efficiently distributed because volumetric distribution was achieved by the lymphatic microcirculatory system surrounding the blood vessel. The behavior of nanoparticle compositions in the adventitial tissue was unknown. The present invention thus differs from methods previously reported in these aspects.

Thus, in some embodiments, there is provided a method of delivering a composition comprising nanoparticles comprising albumin and a macrolide (such as rapamycin) to a blood vessel, wherein the method comprises injecting (for example via a catheter with a needle) into the adventitial tissue of the blood vessel wall an effective amount of a composition comprising nanoparticles comprising a macrolide and an albumin. In some embodiments, there is provided a method of delivering a composition comprising nanoparticles comprising albumin and a macrolide (such as rapamycin) to a blood vessel, wherein the method comprises injecting (for example via a catheter with a needle) into the adventitial tissue of the blood vessel an effective amount of a composition comprising nanoparticles comprising a macrolide and an albumin (such as human serum albumin), wherein the macrolide in the nanoparticles is coated with the albumin. In some embodiments, there is provided a method of delivering a composition comprising nanoparticles comprising albumin and a macrolide (such as rapamycin) to a blood vessel, wherein the method comprises injecting (for example via a catheter with a needle) into the adventitial tissue of the blood vessel an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of delivering a composition comprising nanoparticles comprising albumin and a macrolide (such as rapamycin) to a blood vessel, wherein the method comprises injecting (for example via a catheter with a needle) into the adventitial tissue of the blood vessel an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of delivering Nab-rapamycin to a blood vessel, wherein the method comprises injecting (for example via a catheter with a needle) into the adventitial tissue of the blood vessel wall an effective amount of Nab-rapamycin. In some embodiments, the nanoparticle composition is injected at or adjacent to a disease site (such as no more than about 2, 1, or 0.5 cm away from the disease site). In some embodiments, the nanoparticle composition is injected remotely from a disease site (such example at least about any of 1, 2, 3, 4, 5, 6, 7, 8, 9, or 10 cm away from the disease site). In some embodiments, the nanoparticle composition, upon injection, achieves a volumetric distribution.

The blood vessel described in some embodiments is an artery, such as a coronary artery or a peripheral artery. In some embodiments, the artery is selected from the group consisting of renal artery, cerebral artery, pulmonary artery, and artery in the leg. In some embodiments, the blood vessel is an artery or vein above the knee. In some embodiments, the blood vessel is an artery or vein below the knee. In some embodiments, the blood vessel is a femoral artery. In some embodiments, the blood vessel is a balloon injured artery.

In some embodiments, the blood vessel is an artery selected from any one of the following: abdominal aorta, anterior tibial artery, arch of aorta, arcuate artery, axillary artery, brachial artery, carotid artery, celiac artery, circumflex fibular artery, common hepatic artery, common iliac artery, deep femoral artery, deep palmar arterial arch, dorsal digital artery, dorsal metatarsal artery, external carotid artery, external iliac artery, facial artery, femoral artery, inferior mesenteric artery, internal iliac artery, instestinal artery, lateral inferior genicular artery, lateral superior genicular artery, palmar digital artery, peroneal artery, popliteal artery, posterior tibial artery, profunda femoris artery, pulmonary artery, radial artery, renal artery, splenic artery, subclavian artery, superficial palmar arterial arch, superior mesenteric artery, superior ulnar collateral artery, and ulnar artery.

In some embodiments, the blood vessel is a vein. In some embodiments, the blood vessel is a vein selected from any one of the following: accessory cephalic vein, axillary vein, basilic vein, brachial vein, cephalic vein, common iliac vein, dorsal digital vein, dorsal metatarsal vein, external iliac vein, facial vein, femoral vein, great saphenous vein, hepatic vein, inferior mesenteric vein, inferior vena cava, intermediate antebrachial vein, internal iliac vein, intestinal vein, jugular vein, lateral circumflex femoral vein, left inferior pulmonary vein, left superior pulmonary vein, palmar digital vein, portal vein, posterior tibial vein, renal vein, retromanibular vein, saphenous vein, small saphenous vein, splenic vein, subclavian vein, superior mesenteric vein, and superior vena cava.

In some embodiments, the blood vessel is part of the coronary vasculature (including the arterial and venous vasculature), the cerebral vasculature, the hepatic vasculature, the peripheral vasculature, and the vasculature of other organs and tissue compartments.

In some embodiments, there is provided a method of delivering a composition comprising nanoparticles comprising albumin and a macrolide (such as a rapamycin or a derivative thereof, for example rapamycin) to a blood vessel, wherein the method comprises injecting (for example via a catheter with a needle) periadventitially (i.e., injecting into the periadventitial tissue) to a femoral artery an effective amount of a composition comprising nanoparticles comprising a macrolide and an albumin. In some embodiments, there is provided a method of delivering a composition comprising nanoparticles comprising albumin and a macrolide (such as a rapamycin or a derivative thereof, for example rapamycin) to a blood vessel, wherein the method comprises injecting (for example via a catheter with a needle) periadventitially to a femoral artery an effective amount of a composition comprising nanoparticles comprising a macrolide and an albumin (such as human serum albumin), wherein the macrolide in the nanoparticles is coated with the albumin. In some embodiments, there is provided a method of delivering a composition comprising nanoparticles comprising albumin and a macrolide (such as a rapamycin or a derivative thereof, for example rapamycin) to a blood vessel, wherein the method comprises injecting (for example via a catheter with a needle) periadventitially to a femoral artery an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of delivering a composition comprising nanoparticles comprising albumin and a macrolide (such as a rapamycin or a derivative thereof, for example rapamycin) to a blood vessel, wherein the method comprises injecting (for example via a catheter with a needle) periadventitially to a femoral artery an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of delivering Nab-rapamycin to a blood vessel, wherein the method comprises injecting (for example via a catheter with a needle) periadventitially to a femoral artery an effective amount of Nab-rapamycin. In some embodiments, the nanoparticle composition is injected at or adjacent to a disease site (such as no more than about 2, 1, or 0.5 cm away from the disease site). In some embodiments, the nanoparticle composition is injected remotely from a disease site (such example at least about any of 1, 2, 3, 4, 5, 6, 7, 8, 9, or 10 cm away from the disease site).

The delivery methods described herein are effective in inhibiting one or more aspects of blood vessel abnormalities, including for example, negative remodeling, vascular fibrosis, restenosis, cell proliferation and migration of cells in the blood vessel, and wound healing. In some embodiments, the method is effective in promoting positive remodeling of the blood vessel.

The present application thus in some embodiments provides a method of inhibiting negative remodeling in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of inhibiting negative remodeling in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of inhibiting negative remodeling in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of inhibiting negative remodeling in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provide a method of inhibiting negative remodeling in a blood vessel in an individual in need thereof, comprising injecting into the blood vessel wall or tissue surrounding the blood vessel wall an effective amount of Nab-rapamycin. In some embodiments, the nanoparticle composition is injected at or adjacent to a site of negative remodeling (such as no more than about 2, 1, or 0.5 cm away from the site of negative remodeling). In some embodiments, the nanoparticle composition is injected remotely from a site of negative remodeling (such example at least about any of 1, 2, 3, 4, 5, 6, 7, 8, 9, or 10 cm away from the site of negative remodeling). In some embodiments, the injection is via a catheter with a needle.

Negative remodeling includes the physiologic or pathologic response of a blood vessel to a stimulus resulting in a reduction of vessel diameter and lumen diameter. Such a stimulus could be provided by, for example, a change in blood flow or an angioplasty procedure. In some embodiments, the injection of the nanoparticle composition leads to an increase of vessel diameter by about any of 10%, 20%, 30%, 40%, 60%, 70%, 80%, 95%, or more, compared to the diameter of a vessel of without the injection. Negative remodeling can be quantified, for example, angiographically as the percent diameter stenosis at the lesion site (or disease site). Another method of determining the degree of remodeling involves measuring in-lesion external elastic lamina area using intravascular ultrasound (IVUS). IVUS is a technique that can image the external elastic lamina as well as the vascular lumen. In some embodiments, the negative remodeling is associated with a vascular interventional procedure, such as angioplasty, stenting, or atherectomy. The nanoparticle composition can therefore be injected during or after the vascular interventional procedure.

In some embodiments, there is provided a method of promoting positive remodeling in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of promoting positive remodeling in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of promoting positive remodeling in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of promoting positive remodeling in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provide a method of promoting positive remodeling in a blood vessel in an individual in need thereof, comprising injecting into the blood vessel wall or tissue surrounding the blood vessel wall an effective amount of Nab-rapamycin. In some embodiments, the nanoparticle composition is injected at or adjacent to a site of negative remodeling (such as no more than about 2, 1, or 0.5 cm away from the site of negative remodeling). In some embodiments, the nanoparticle composition is injected remotely from a site of negative remodeling (such example at least about any of 1, 2, 3, 4, 5, 6, 7, 8, 9, or 10 cm away from the site of negative remodeling). In some embodiments, the injection is via a catheter with a needle.

Positive remodeling used herein refers to an increase of vessel diameter as compared to the diameter of a vessel without the injection. In some embodiments, the injection of the nanoparticle composition leads to an increase of vessel diameter by about any of 10%, 20%, 30%, 40%, 60%, 70%, 80%, 95%, or more, compared to the diameter of a vessel of without the injection.

In some embodiments, there is provided a method of inhibiting vascular fibrosis (such as medial vascular fibrosis) in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of inhibiting vascular fibrosis (such as medial vascular fibrosis) in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of inhibiting vascular fibrosis (such as medial vascular fibrosis) in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of inhibiting vascular fibrosis (such as medial vascular fibrosis) in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of inhibiting vascular fibrosis (such as medial vascular fibrosis) in a blood vessel in an individual in need thereof, comprising injecting into the blood vessel wall or tissue surrounding the blood vessel wall an effective amount of Nab-rapamycin. In some embodiments, the nanoparticle composition is injected at or adjacent to the site of vascular fibrosis (for example no greater than about any of 2, 1, 0.5 cm away from the site of vascular fibrosis). In some embodiments, the nanoparticle composition is injected remotely from a site of vascular fibrosis (such example at least about any of 2, 3, 4, 5, 6, 7, 8, 9, or 10 cm away from the site of vascular fibrosis). In some embodiments, the injection is via a catheter with a needle.

Vascular fibrosis as used herein refers to the extensive fibrous (connective) tissue formation in the blood vessel, and includes, for example, medial fibrosis or adventitial fibrosis. Vascular fibrosis is frequently associated with abundant deposition of extracellular matrix and proliferation of myofibroblasts and fibroblasts. The method described herein therefore in some embodiments inhibits fibrous tissue formation in the blood vessel, for example inhibits about any of 10%, 20%, 30%, 40%, 50%, 60%, 70%, 80%, or 90% fibrous tissue formation compared to a vessel without the injection. In some embodiments, the method inhibits deposition of extracellular matrix in the blood vessel, for example inhibits about any of 10%, 20%, 30%, 40%, 50%, 60%, 70%, 80%, or 90% deposition of extracellular matrix compared to a vessel without the injection. In some embodiments, the method inhibits proliferation of myofibroblast in the blood vessel, for example inhibits about any of 10%, 20%, 30%, 40%, 50%, 60%, 70%, 80%, or 90% proliferation of myofibroblast compared to a vessel without the injection. In some embodiments, the method inhibits proliferation of fibroblast in the blood vessel, for example inhibits about any of 10%, 20%, 30%, 40%, 50%, 60%, 70%, 80%, or 90% proliferation of fibroblast compared to a vessel without the injection. In some embodiments, the vascular fibrosis is associated with a vascular interventional procedure, such as angioplasty, stenting, or atherectomy. The nanoparticle composition can therefore be injected during or after the vascular interventional procedure.

The method described herein therefore in some embodiments inhibits luminal stenosis, for example inhibits about any of 10%, 20%, 30%, 40%, 50%, 60%, 70%, 80%, or 90% luminal stenosis compared to a vessel without the injection. In some embodiments, the luminal stenosis is associated with a vascular interventional procedure, such as angioplasty, stenting, or atherectomy. The nanoparticle composition can therefore be injected during or after the vascular interventional procedure.

In some embodiments, there is provided a method of treating restenosis in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of treating restenosis in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of treating restenosis in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of treating restenosis in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of treating restenosis in a blood vessel in an individual in need thereof, comprising injecting into the blood vessel wall or tissue surrounding the blood vessel wall an effective amount of Nab-rapamycin. In some embodiments, the nanoparticle composition is injected at or adjacent to a disease site (for example no more than about 2, 1, or 0.5 cm away from the disease site). In some embodiments, the nanoparticle composition is injected remotely from a disease site (such example at least about any of 1, 2, 3, 4, 5, 6, 7, 8, 9, or 10 cm away from the disease site). In some embodiments, the injection is via a catheter with a needle.

In some embodiments, there is provided a method of reducing adventitial leukocytes in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of reducing adventitial leukocytes in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of reducing adventitial leukocytes in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of reducing adventitial leukocytes in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of reducing adventitial leukocytes in a blood vessel in an individual in need thereof, comprising injecting into the blood vessel wall or tissue surrounding the blood vessel wall an effective amount of Nab-rapamycin. In some embodiments, the nanoparticle composition is injected into the adventitial tissue.

In some embodiments, there is provided a method of reducing adventitial vessels in a blood vessel in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of reducing adventitial vessels in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of reducing adventitial vessels in a blood vessel in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of reducing adventitial vessels in a blood vessel in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of reducing adventitial vessels in a blood vessel in an individual in need thereof, comprising injecting into the blood vessel wall or tissue surrounding the blood vessel wall an effective amount of Nab-rapamycin. In some embodiments, the nanoparticle composition is injected into the adventitial tissue.

In some embodiments, the individual is human. In some embodiments, the individual is at least about any of 35, 40, 45, 50, 55, 60, 65, 70, 75, 80, or 85 years old. In some embodiments, the individual is of Asian ancestry. In some embodiments, the individual is a male. In some embodiments, the individual is a female. In some embodiments, the individual has a disease as discussed below.

The methods described herein are useful for treating a variety of diseases. These include, for example, angina, aortic stenosis, arteriosclerosis obliterans, carotid artery stenosis, cerebrovascular artery disease, cerebrovascular occlusive disease, coronary artery disease, dilated cardiomyopathy, cardiomyopathy, ischemic cardiomyopathy, intermittent claudication, peripheral artery stenosis, renal artery disease, restenosis, small vessel disease, stenosis, aortic stenosis, Aortic valve stenosis, hyaline arteriolosclerosis, hyperplastic arteriosclerosis, mitrial stenosis, pulmonary valve stenosis, tricuspid valve stenosis, deep vein thrombosis, peripheral venous disease, and thrombophlebitis. The methods described herein may encompass the treatment of any one or more of these diseases.

In some embodiments, the disease is selected from the group consisting of angina, myocardial infarction, congestive heart failure, cardiac arrhythmia, peripheral artery disease, claudication, or chronic limb ischemia. Thus, for example, in some embodiments, there is provided a method of treating angina (or myocardial infarction, or congestive heart failure, or cardiac arrhythmia, or peripheral artery disease, or claudication, or chronic limb ischemia) in an individual in need thereof, comprising injecting into the blood vessel wall or tissue surrounding the blood vessel wall an effective amount of a composition comprising nanoparticles comprising a macrolide (such as rapamycin) and an albumin. In some embodiments, there is provided a method of treating angina (or myocardial infarction, or congestive heart failure, or cardiac arrhythmia, or peripheral artery disease, or claudication, or chronic limb ischemia) in an individual in need thereof, comprising injecting into the blood vessel wall or tissue surrounding the blood vessel wall an effective amount of a composition comprising nanoparticles comprising a macrolide and an albumin (such as human serum albumin), wherein the macrolide in the nanoparticles is coated with the albumin. In some embodiments, there is provided a method of treating angina (or myocardial infarction, or congestive heart failure, or cardiac arrhythmia, or peripheral artery disease, or claudication, or chronic limb ischemia) in an individual in need thereof, comprising injecting into the blood vessel wall or tissue surrounding the blood vessel wall an effective amount of a composition comprising nanoparticles comprising a macrolide and an albumin (such as human serum albumin), wherein the average particle size of the nanoparticles in the composition is no greater than about 200 nm (such as less than about 200 nm, for example no greater than about 100 nm). In some embodiments, there is provided a method of treating angina (or myocardial infarction, or congestive heart failure, or cardiac arrhythmia, or peripheral artery disease, or claudication, or chronic limb ischemia) in an individual in need thereof, comprising injecting into the blood vessel wall or tissue surrounding the blood vessel wall an effective amount of a composition comprising nanoparticles comprising rapamycin and an albumin (such as human serum albumin), wherein the rapamycin in the nanoparticles is coated with the albumin, and wherein the average particle size of the nanoparticles in the composition is no greater than about 200 nm (such as less than about 200 nm for example no greater than about 100 nm). In some embodiments, there is provided a method of treating angina (or myocardial infarction, or congestive heart failure, or cardiac arrhythmia, or peripheral artery disease, or claudication, or chronic limb ischemia) in an individual in need thereof, comprising injecting into the blood vessel wall or tissue surrounding the blood vessel wall an effective amount of Nab-rapamycin. In some embodiments, the nanoparticle composition is injected at or adjacent to a disease site (for example no more than about 2, 1, or 0.5 cm away from the disease site). In some embodiments, the nanoparticle composition is injected remotely from a disease site (such example at least about any of 1, 2, 3, 4, 5, 6, 7, 8, 9, or 10 cm away from the disease site). In some embodiments, the injection is via a catheter with a needle. In some embodiments, the nanoparticle composition is injected during or after the vascular interventional procedure, such as angioplasty, stenting, or atherectomy.

The methods described herein in some embodiments comprise injecting the nanoparticle composition distal to the disease site. In some embodiments, the nanoparticle composition is injected proximal to the disease site. The delivery site may be located within the same blood vessel as the disease treatment region at a location which is longitudinally spaced-apart from the region, or may be located in a different blood vessel. In some embodiments, the nanoparticle composition is injected at or adjacent to the disease site (for example no more than about any of 2, 1, or 0.5 cm away (for example longitudinally away) from the disease site). In some embodiments, the nanoparticle composition is injected remotely from the disease site (for example about any of 1, 2, 3, 4, 5, 6, 7, 8, 9, or 10 cm away (for example longitudinally away) from the disease site). In some embodiments, the disease treatment region may have been previously stented where the delivery site is spaced away from the stent, either longitudinally away from the stent in the same coronary artery or remote from the stent in another coronary artery or vein.

The methods described herein in some embodiments comprise injecting the nanoparticle composition with a needle (such as a deployable needle). The needle can be positioned such that the nanoparticle composition is delivered to a desired site. The methods in some embodiments thus comprise positioning a needle through the wall of a blood vessel and delivering an effective amount of the nanoparticle composition into the wall of the blood vessel or the tissue surrounding the blood vessel wall. For example, in some embodiments, the aperture of the needle lies beyond the external elastic lamina of the blood vessel so that the nanoparticle composition is delivered to the adventitial tissue surrounding the blood vessel. In some embodiments, the aperture of the needle is positioned at a distance that is no more than about 0.1 mm, about 0.2 mm, 0.5 mm, 0.8 mm, 1 cm, 2 cm, 3 cm, 4 cm, 5 cm, 6 cm, 7 cm, or 8 cm beyond the external elastic lamina of the blood vessel.

In some embodiments, the aperture is positioned at a distance from the inner wall of the blood vessel that is at least about 10% (including for example at least about 20%, 30%, 40%, 60%, 70%, 80%, 90%) of the mean luminal diameter of the blood vessel at the injection site. In some embodiments, the aperture is positioned at a distance from the inner wall of the blood vessel that is about 10% to about 75% (including for example about 20% to about 60%, about 30% to about 50%) of the mean luminal diameter of the blood vessel at the injection site.

Confirmation of the position of the needle aperture can be achieved in a variety of ways. For example, a bolus of contrast agent or other visible media can be injected through the needle after initial positioning of the needle is achieved. By observing the distribution of the media, for example fluroscopically, the position of the aperture can be assessed. In some embodiments, various sensors can be attached or otherwise coupled to the needle, usually near the delivery aperture, in order to detect the position of the needle. Exemplary sensors include temperature sensors, pH sensors, electrical impedance sensors, and the like. It is also possible to measure the back pressure on an injected suspension in order to determine the needle position. Injection into the blood vessel wall will typically result in a greater back pressure than injection into the adventitial space. It is also possible to monitor the insertion force of the needle, e.g., by providing a deflection gauge on a portion of the needle.

Dosing and Method of Administering the Nanoparticle Compositions

The dose of the macrolide nanoparticle compositions injected to an individual (such as a human) may vary with the type of blood vessel for the injection, the purpose of the method, and the type of disease being treated. In some embodiments, the amount of the macrolide nanoparticle composition injected is sufficient to inhibit negative remodeling by more than about any of 5%, 10%, 15%, 20%, 25%, 30%, 35%, 40%, 45%, 50%, 55%, 60%, 64%, 65%, 70%, 75%, 80%, 85%, or 90%. Inhibition of negative remodeling can be assessed, for example, by measuring the vessel or luminal diameter of the blood vessel. In some embodiments, the amount of the macrolide nanoparticle composition injected is sufficient to promote positive remodeling by more than about any of 5%, 10%, 15%, 20%, 25%, 30%, 35%, 40%, 45%, 50%, 55%, 60%, 64%, 65%, 70%, 75%, 80%, 85%, or 90%.

In some embodiments, the amount of the macrolide nanoparticle composition injected is sufficient to inhibit vascular fibrosis by more than about any of 5%, 10%, 15%, 20%, 25%, 30%, 35%, 40%, 45%, 50%, 55%, 60%, 64%, 65%, 70%, 75%, 80%, 85%, or 90%. In some embodiments, the vascular fibrosis is medial fibrosis. In some embodiments, the vascular fibrosis is adventitial fibrosis. Inhibition of vascular fibrosis can be assessed, for example, by evaluating the amount of extracellular matrix deposition and/or proliferation of myofibroblasts and fibroblasts. In some embodiments, the vascular fibrosis is evaluated by histopathology analysis, for example by staining with H&E or trichrome.

In some embodiments, the amount of the macrolide nanoparticle composition injected is sufficient to reduce proliferation index by more than about any of 5%, 10%, 15%, 20%, 25%, 30%, 35%, 40%, 45%, 50%, 55%, 60%, 64%, 65%, 70%, 75%, 80%, 85%, or 90%. In some embodiments, the amount of the macrolide nanoparticle composition injected is sufficient to reduce luminal stenosis by more than about any of 5%, 10%, 15%, 20%, 25%, 30%, 35%, 40%, 45%, 50%, 55%, 60%, 64%, 65%, 70%, 75%, 80%, 85%, or 90%. In some embodiments, the amount of the macrolide nanoparticle composition injected is sufficient to reduce adventitial leukocytes by more than about any of 5%, 10%, 15%, 20%, 25%, 30%, 35%, 40%, 45%, 50%, 55%, 60%, 64%, 65%, 70%, 75%, 80%, 85%, or 90%. In some embodiments, the amount of the macrolide nanoparticle composition injected is sufficient to reduce adventitial vessels by more than about any of 5%, 10%, 15%, 20%, 25%, 30%, 35%, 40%, 45%, 50%, 55%, 60%, 64%, 65%, 70%, 75%, 80%, 85%, or 90%.

In some embodiments, the amount of the macrolide (e.g., rapamycin) in the composition is below the level that induces a toxicological effect (i.e., an effect above a clinically acceptable level of toxicity) or is at a level where a potential side effect can be controlled or tolerated when the composition is injected to the individual.

In some embodiments, the amount of a macrolide (e.g., rapamycin or derivative thereof, for example rapamycin) per injection is within any one of the following ranges: about 0.001 to about 100 mg, including for example about 0.001 to about 0.005 mg, about 0.005 to about 0.025 mg, about 0.025 to about 0.1 mg, about 0.1 to about 0.5 mg, about 0.5 to about 1 mg, about 1 to about 2 mg, about 2 to about 3 mg, about 3 to about 4 mg, about 4 to about 5 mg, about 5 to about 6 mg, about 6 to about 7 mg, about 7 to about 8 mg, about 8 to about 9 mg, about 9 to about 10 mg, about 10 to about 15 mg, about 15 to about 20 mg, about 20 to about 25 mg, about 20 to about 50 mg, about 25 to about 50 mg, about 50 to about 75 mg, or about 50 to about 100 mg. In some embodiments, the amount of a macrolide (e.g., rapamycin) per injection is in the range of about 0.001 to about 100 mg, such as about 0.005 to about 80 mg, about 0.05 to about 50 mg, about 0.1 to about 10 mg, about 0.1 to about 5 mg, about 0.5 to about 5 mg, about 0.05 to about 5 mg, or about 0.5 to about 2 mg.

In some embodiments, the concentration of the macrolide (e.g., rapamycin) in the nanoparticle composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the macrolide (e.g., rapamycin) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. In some embodiments, the concentration of the macrolide (e.g., rapamycin) is no more than about any of 100 mg/ml, 90 mg/ml, 80 mg/ml, 70 mg/ml, 60 mg/ml, 50 mg/ml, 40 mg/ml, 30 mg/ml, 20 mg/ml, 10 mg/ml, or 5 mg/ml.

The volume of the nanoparticle composition per injection may vary with the type of blood vessel for the injection, the purpose of the method, and the type of disease being treated. In some embodiments, the volume per injection is about 0.01 to about 50 ml, including for example about 0.01 to about 0.05 ml, about 0.05 to about 0.1 ml, about 0.1 to about 0.5 ml, about 0.5 to about 1 ml, about 1 to about 2 ml, about 2 to about 3 ml, about 3 to about 5 ml, about 5 to about 10 ml, about 10 to about 20 ml, about 20 to about 30 ml, about 30 to about 40 ml, about 40 to about 50 ml. In some embodiments, the volume per injection is about 0.05 to about 2 ml, about 0.1 to 1 ml, about 0.25 to about 0.5 ml, or about 0.5 to about 1 ml, or about 1 to about 5 ml.

Exemplary dosing frequencies for the administration of the nanoparticle compositions include, but are not limited to, about once every 1, 2, 3, 4, 5, 6, 7, 8, 9, 10, 11, or 12 months. In some embodiments, the intervals between each administration are more than about any of 1 month, 2 months, 3 months, 4 months, 5 months, 6 months, 8 months, or 12 months. In some embodiments, the administration is administered every 3, 6, 9, 12, 15, 18, 21, or 24 months. In some embodiments, the administration is administered at most every 3, 6, 9, 12, 15, 18, 21, or 24 months. In some embodiments, the administration is administered at least every 3, 6, 9, 12, 15, 18, 21, or 24 months. In some embodiments, the nanoparticle composition is injected only once.

The nanoparticle composition can be injected during a vascular interventional procedure. In some embodiments, the nanoparticle composition is injected once during the vascular interventional procedure. In some embodiments, the nanoparticle composition is injected after a vascular interventional procedure. Exemplary vascular interventional procedures include, but are not limited to, angioplasty, stenting, and atherectomy.

Nanoparticle Compositions

The nanoparticle compositions described herein comprise nanoparticles comprising (in various embodiments consisting essentially of or consisting of) a macrolide (such as rapamycin) and an albumin (such as human serum albumin). Nanoparticles of poorly water soluble drugs (such as macrolide) have been disclosed in, for example, U.S. Pat. Nos. 5,916,596; 6,506,405; 6,749,868, 6,537,579, 7,820, 788, and also in U.S. Pat. Pub. Nos. 2006/0263434, and 2007/0082838; PCT Patent Application WO08/137148, each of which is incorporated by reference in their entirety.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the average or mean diameter of the nanoparticles is about 50 to about 100 nm. In some embodiments, the nanoparticles are no less than about 50 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm.

In some embodiments, the nanoparticles in the composition described herein have an average diameter of no less than about 50 nm, including for example no less than about any one of 50, 60, 70, 80, 90, or 100 nm. In some embodiments, at least about 50% (for example at least about any one of 60%, 70%, 80%, 90%, 95%, or 99%) of the nanoparticles in the composition have a diameter of no less than about 50 nm, including for example no less than about any one of 50, 60, 70, 80, 90, or 100 nm.

In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the albumin has sulfhydral groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise the macrolide (such as rapamycin) coated with an albumin (e.g., human serum albumin). In some embodiments, the composition comprises a macrolide in both nanoparticle and non-nanoparticle forms (e.g., in the form of rapamycin solutions or in the form of soluble albumin/nanoparticle complexes), wherein at least about any one of 50%, 60%, 70%, 80%, 90%, 95%, or 99% of the macrolide in the composition are in nanoparticle form. In some embodiments, the macrolide in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of a macrolide that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and a macrolide in the nanoparticle composition is about 18:1 or less, such as about 15:1 or less, for example about 10:1 or less. In some embodiments, the weight ratio of albumin (such as human serum albumin) and macrolide in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and macrolide in the nanoparticle portion of the composition is about any one of 1:2, 1:3, 1:4, 1:5, 1:10, 1:15, or less. In some embodiments, the weight ratio of the albumin (such as human serum albumin) and the macrolide in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of macrolides, especially neutral and negatively charged hydrophobic compounds (Goodman et al., *The Pharmacological Basis of Therapeutics*, 9$^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Rapamycin and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The albumin (such as human serum albumin) in the composition generally serves as a carrier for the macrolide, i.e., the albumin in the composition makes the macrolide more readily suspendable in an aqueous medium or helps maintain the suspension as compared to compositions not comprising an albumin. This can avoid the use of toxic solvents (or surfactants) for solubilizing the macrolide, and thereby can reduce one or more side effects of administration of the macrolide into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is injected to the individual. In some embodiments, the nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize the macrolide in an aqueous suspension, for example, in the form of a stable colloidal suspension (such as a stable suspension of nanoparticles). In some embodiments, the albumin is in an amount that reduces the sedimentation rate of the macrolide in an aqueous medium. For particle-containing compositions, the amount of the albumin also depends on the size and density of nanoparticles of the macrolide.

A macrolide is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the macrolide in an aqueous suspension at a certain concentration. For example, the concentration of the macrolide in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the macrolide is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to the macrolide in the nanoparticle composition is such that a sufficient amount of macrolide binds to, or is transported by, the cell. While the weight ratio of albumin to macrolide will have to be optimized for different albumin and macrolide combinations, generally the weight ratio of albumin, e.g., albumin, to macrolide (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to macrolide weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) to the macrolide in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1.

In some embodiments, the albumin allows the composition to be injected to an individual (such as human) without significant side effects. In some embodiments, the albumin (such as human serum albumin) is in an amount that is effective to reduce one or more side effects of administration of the macrolide to a human. The term "reducing one or more side effects of administration of the macrolide" refers to reduction, alleviation, elimination, or avoidance of one or more undesirable effects caused by the macrolide, as well as side effects caused by delivery vehicles (such as solvents that render the macrolides suitable for injection) used to deliver the macrolide. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with macrolides can be reduced.

In some embodiments, the nanoparticle composition comprises Nab-rapamycin (Celgene Corp.). In some embodiments, the nanoparticle composition is Nab-rapamycin. Nab-rapamycin is a formulation of rapamycin stabilized by human albumin USP, which can be dispersed in directly injectable physiological solution. When dispersed in a suitable aqueous medium such as 0.9% sodium chloride injection or 5% dextrose injection, Nab-rapamycin forms a stable colloidal suspension of rapamycin. The mean particle size of the nanoparticles in the colloidal suspension is about 90 nanometers. Since HSA is freely soluble in water, Nab-rapamycin can be reconstituted in a wide range of concentrations ranging from dilute (0.1 mg/ml rapamycin) to concentrated (20 mg/ml rapamycin), including for example about 2 mg/ml to about 8 mg/ml, or about 5 mg/ml.

Methods of making nanoparticle compositions are known in the art. For example, nanoparticles containing macrolides (such as rapamycin) and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO08/137148.

Briefly, the macrolide (such as rapamycin) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that include other agents, excipients, or stabilizers. For example, to increase stability by increasing the negative zeta potential of nanoparticles, one or more of negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyri stoylphosphatidylcholine (DMPC), dioleoylphosphatidylcholine (DOPC), di stearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596, 6,096,331, and 7,820,788). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration such as injection include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits and Devices

The invention also provides kits and devices for use in any of the methods described herein.

For example, in some embodiments, there is provided a catheter with a needle (such as a deployable needle), wherein the needle contains a composition comprising nanoparticle comprising a macrolide (such as rapamycin) and an albumin. In some embodiments, there is provided a catheter with a needle (such as a deployable needle), wherein the needle contains a composition comprising nanoparticle comprising a macrolide (such as rapamycin) coated with an albumin. In some embodiments, there is provided a catheter with a needle (such as a deployable needle), wherein the needle contains a composition comprising nanoparticle comprising a macrolide (such as rapamycin) and an albumin, wherein the average particle size of the nanoparticles in the composition is no greater than about 200 nm (such as less than about 200 nm, for example no greater than about 100 nm). In some embodiments, there is provided a catheter with a needle (such as a deployable needle), wherein the needle contains a composition comprising nanoparticle comprising a macrolide (such as rapamycin) coated with an albumin, wherein the average particle size of the nanoparticles in the composition is no greater than about 200 nm (such as less than about 200 nm, for example no greater than about 100 nm). In some embodiments, there is provided a catheter with a needle (such as a deployable needle), wherein the needle contains Nab-rapamycin. In some embodiments, the needle is sheathed in a balloon. In some embodiments the diameter of the needle is about 0.1 to about 3 mm, including for example about 0.2 to about 2 mm, about 0.5 to about 1 mm, about 0.6 to about 0.9 mm, or about 0.9 mm. The length of the needle is typically between about 20 and 3000 microns, including for example between about 20-50, about 50-100, about 100-200, about 200-300, about 300-400, about 400-500, about 500-600, about 600-700, about 700-800, about 800-900, about 1-2, and about 2-3 microns. In some embodiments, the catheter contains more than 1 (such as 2, 3, 4, 5, 6, 7, or more) needles.

Also provided are kits comprising one or more containers comprising macrolide-containing nanoparticle compositions (or unit dosage forms and/or articles of manufacture) and in some embodiments, further comprise instructions for use in accordance with any of the methods described herein. In some embodiments, the kit comprises a catheter having a needle which can be advanced from a blood vessel lumen through a wall of the blood vessel (for example to position an aperture of the needle beyond an external elastic lamina of the wall), and a nanoparticle composition comprising a macrolide and albumin, wherein the nanoparticle composition is injectable through the needle. In some embodiments, the kit further comprises a syringe. In some embodiments, the syringe is filled up with an effective amount of the nanoparticle composition.

The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the nanoparticle compositions generally include information as to dosage, dosing schedule, and specific instructions on delivering the nanoparticle composition. The containers may be unit doses, bulk packages (e.g., multi-dose packages) or sub-unit doses. Kits may also include multiple unit doses of the macrolide and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1. Method for Periadventitial Injection with Micro-Infusion Catheter

This example demonstrates the injection of Nab-rapamycin into the periadventitial tissue. Nab-rapamycin (Celgene Corporation) was reconstituted in saline to 5 mg/ml prior to the injection.

Figure 1B:
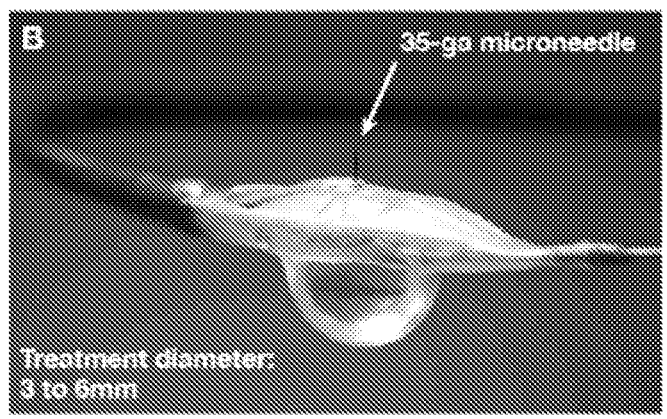

To inject Nab-rapamycin into the periadventitial tissue, the Bullfrog® Micro-Infusion Catheter (Mercator Medsystems, San Leandro Calif.) was introduced into the artery while deflated and with the 0.9 mm needle sheathed within a balloon (FIG. 1A). When the balloon was inflated, the needle extruded outward, perpendicular to the axis of the catheter while a backing balloon provided an opposing force to slide the needle into the artery wall (FIG. 1B). Nab-rapamycin was then delivered into the periadventitial tissue through the needle.

Example 2. Periadventitial Delivery of Nab-Rapamycin in a Porcine Femoral Artery Balloon Injury Model This experiment was conducted to determine whether periadventitial delivery of Nab-rapamycin can decrease luminal stenosis in a porcine femoral artery balloon angioplasty injury model.

Figure 2A:
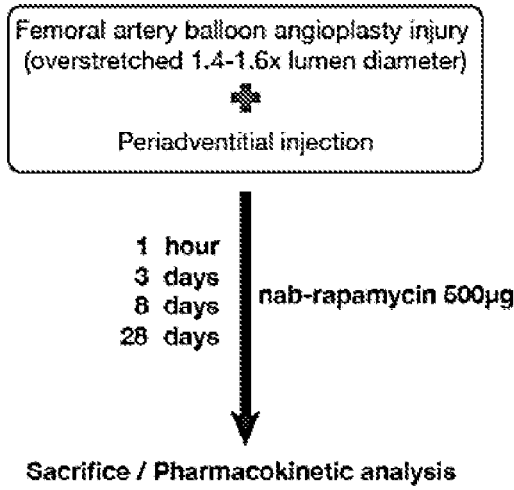
FIGS. 2A and 2B provide two flow charts for the study design involving periadventitial injection of Nab-rapamycin in a porcine femoral artery balloon angioplasty injury model.
Figure 2B:
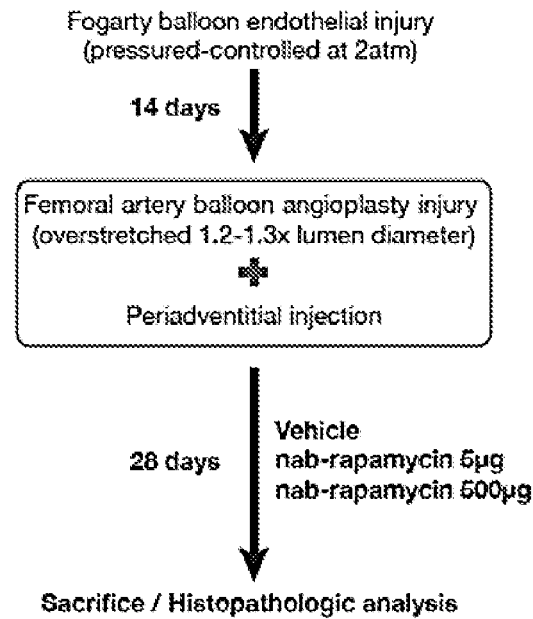

Sixteen juvenile male Yorkshire cross pigs (average weight 34.9±2.3 kg) were used in 2 study arms (FIGS. 2A and 2B). After induction of general anesthesia, percutaneous access was obtained via the carotid artery. Animals were given intravenous heparin (5000 units). All pigs were maintained on aspirin 81 mg daily after the procedure. Femoral arteries were flushed with 1 liter lactated Ringer's solution after sacrifice. Arteries were then harvested (pharmacokinetics arm) or subsequently perfusion fixed at 120 mmHg for 10 minutes with 10% buffered formalin before harvest (histopathology arm).

Figure 3A:
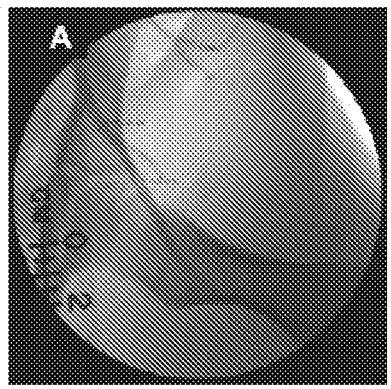
FIGS. 3A, 3B, 3C, 3D, 3E, and 3F show a representative angiogram series for periadventitial injection of Nab-rapamycin in the femoral artery.
Figure 3B:
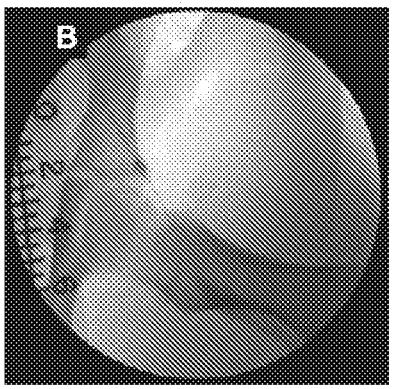
Figure 3C:
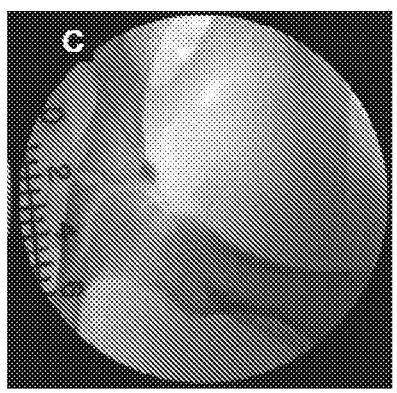
Figure 3D:
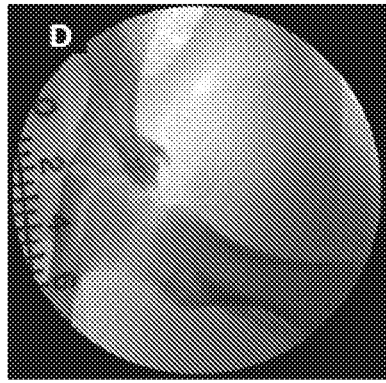
Figure 3E:
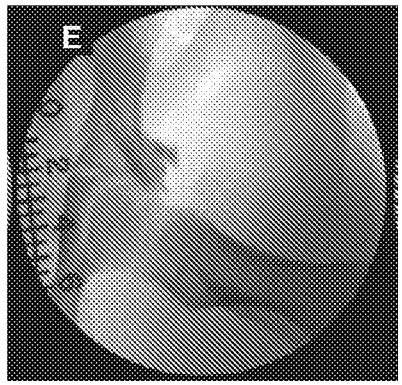
Figure 3F:
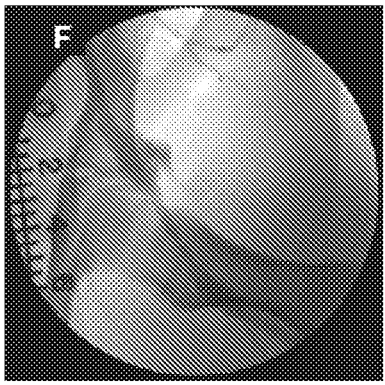

Nab-rapamycin was injected by periadventitial injection. An initial diagnostic angiogram showed the target femoral artery diameter was 4 mm (FIG. 3A). The micro-infusion catheter was positioned in the mid-femoral artery and the balloon was inflated (FIG. 3B). A periadventitial injection of Nab-rapamycin solution with 20% iodinated contrast (Iso-Vue 370) showed circumferential coverage of the vessel (FIGS. 3C-3E). Completion angiogram revealed a patent femoral artery (FIG. 3F). There was 100% procedural success with 32 injection sites. Average injection time was 90 seconds (1 ml/min). There were no dissections, early or late thromboses, hemorrhages or arteriovenous fistulas.

Figure 4A:
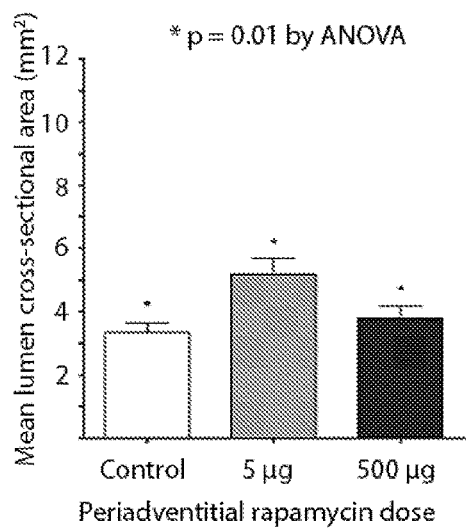
FIGS. 4A, 4B, 4C, and 4D show reduction of luminal stenosis after periadventitial delivery of Nab-rapamycin as measured by mean lumen cross-sectional area (FIG. 4A), mean artery cross sectional area (FIG. 4B), mean percent luminal stenosis (FIG. 4C), and average medial fibrosis (FIG. 4D).
Figure 4B:
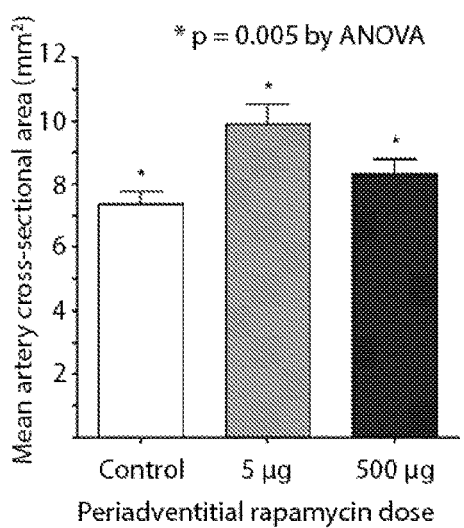
Figure 4C:
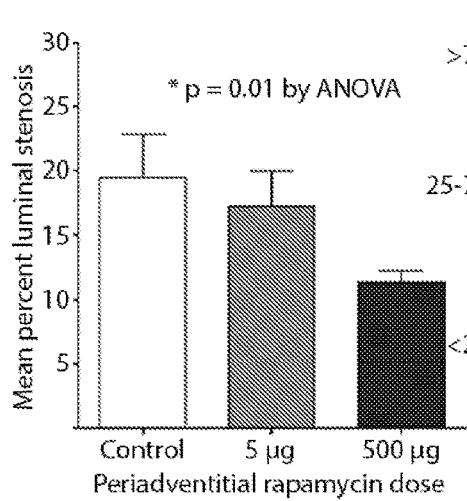
Figure 4D:
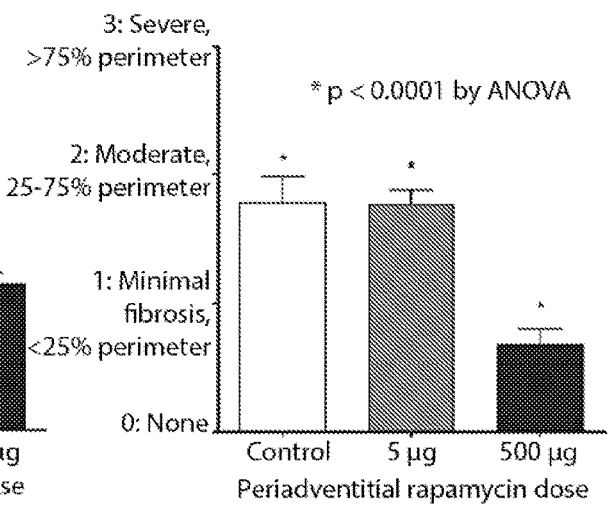

Histomorphometry results after periadventitial injection of Nab-rapamycin in the femoral artery were analyzed. Femoral arteries treated with periadventitial Nab-rapamycin had significantly larger lumen cross-sectional areas p=0.01 (ANOVA)(FIG. 4A), as well as significantly larger total vessel cross-sectional areas (FIG. 4B), p=0.005 (ANOVA) at 28 days after treatment. There was a trend toward decreasing percent luminal stenosis with Nab-rapamycin treatment at 28 days. Femoral arteries treated with periadventitial Nab-rapamycin (500 □ g) had a 42% reduction in luminal stenosis at 28 days (19.5+3% vs 11.4+0.8%, p=0.01 t-test) (FIG. 4C). The average medial fibrosis score at 28 days was significantly less in the Nab-rapamycin treated arteries compared to control arteries treated with vehicle alone (FIG. 4D), p<0.0001 (ANOVA).

Figure 5A:
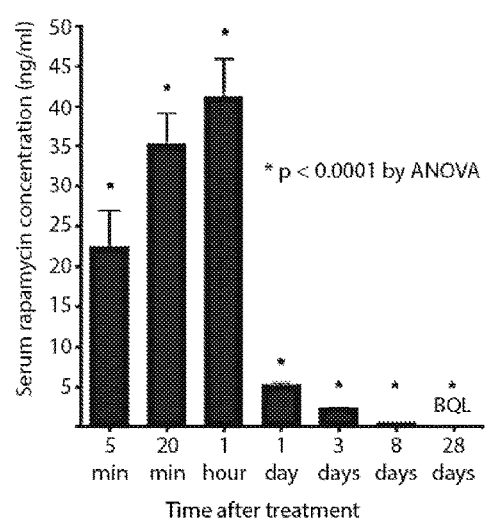
FIGS. 5A and 5B show the pharmacokinetics of Nab-rapamycin after periadventitial delivery in femoral arteries as measured by serum rapamycin concentration (FIG. 5A) and tissue rapamycin concentration (FIG. 5B).
Figure 5B:
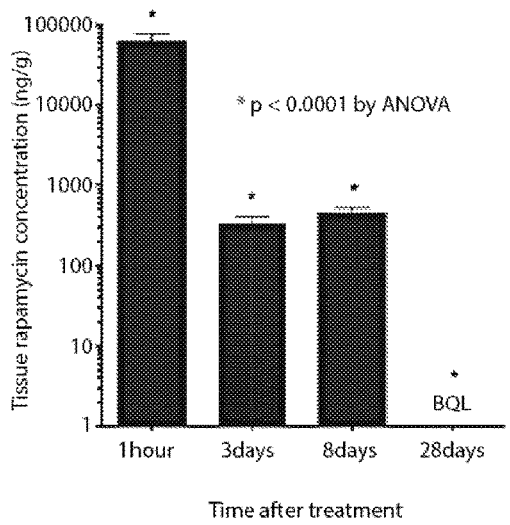

Pharmacokinetic results after periadventitial injection of Nab-rapamycin in the femoral artery were analyzed. Blood (serum) rapamycin levels rose in the first hour after a single periadventitial injection of Nab-rapamycin at 500 µg, but fell by 1 day and were not detectable by 28 days (FIG. 5A). In the femoral artery and surrounding perivascular tissue, the rapamycin concentration was over 1500-times the serum concentration at 1 hour. Rapamycin persisted over 8 days and was not detectable by 28 days (FIG. 5B).

Figure 6A:
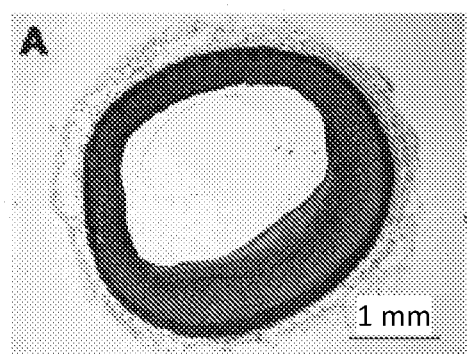
FIGS. 6A, 6B, 6C, and 6D show histopathology staining of femoral arteries treated with vehicle (FIGS. 6C and 6D) or with Nab-rapamycin (FIGS. 6A and 6B) by periadventitial delivery.
Figure 6B:
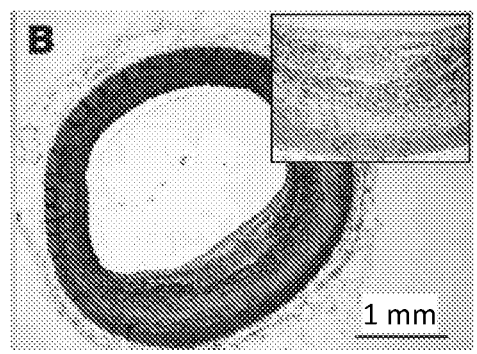
Figure 6C:
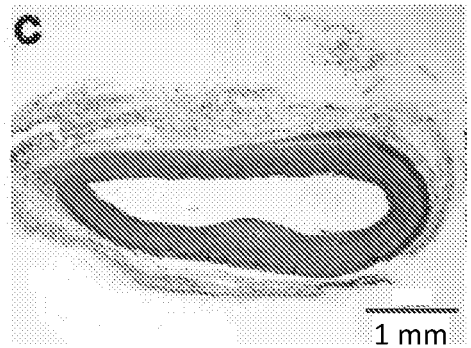
Figure 6D:
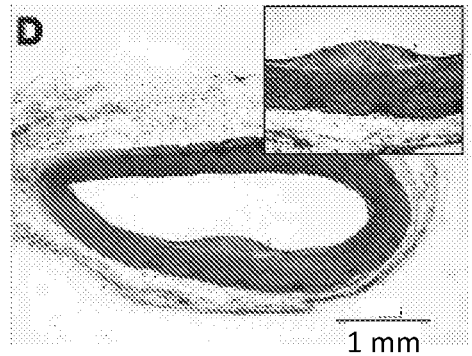

Histopathology results after periadventitial injection of Nab-rapamycin in the femoral artery were analyzed. FIGS. 6A-6D show representative sections of femoral arteries 28 days after treatment with vehicle (FIGS. 6A and 6B) or Nab-rapamycin 500 µg (FIGS. 6C and 6D). Nab-rapamycin treatment was associated with significantly reduced medial fibrosis with similar degrees of internal elastic lamina injury (inset, 100×). Vessels were stained with H&E (FIGS. 6A and 6C) and trichrome (FIGS. 6B and 6D) and imaged at 25×.

Figure 7A:
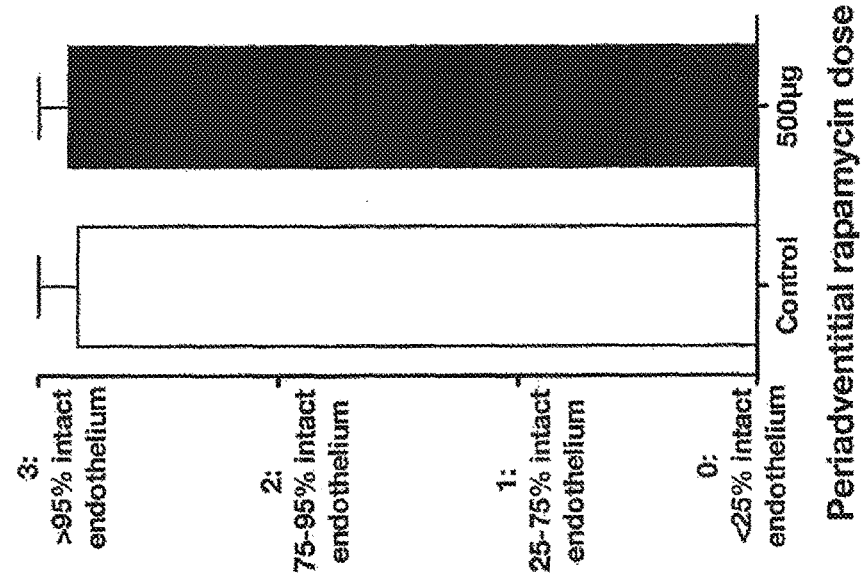
FIG. 7A shows the proliferative index after periadventitial delivery of Nab-rapamycin or a control.
Figure 7B:
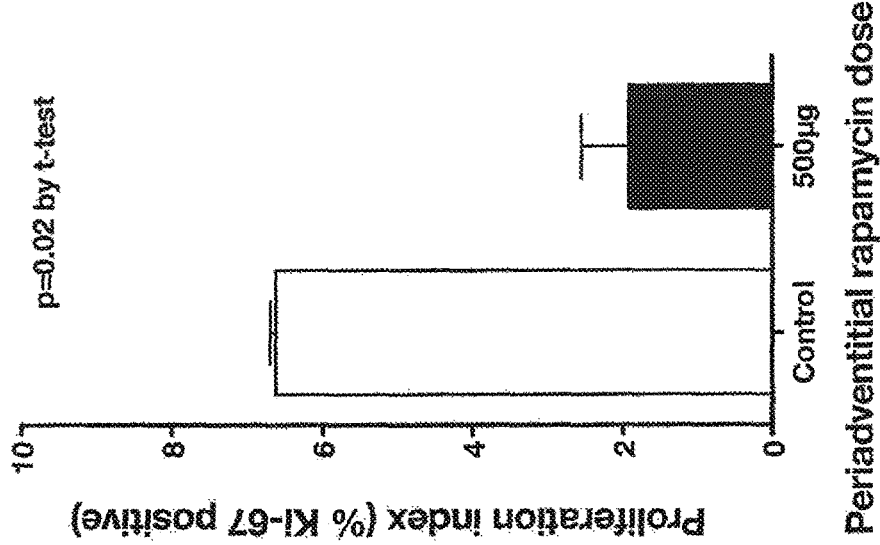
FIG. 7B shows the endothelialization after periadventitial delivery of Nab-rapamycin or a control.

Further histomorphometry analyses showed that Nab-rapamycin treatment was associated with significantly reduced proliferation index (FIG. 7A). On the other hand, there was no difference in endothelization at 28 days in control and Nab-rapamycin treated femoral arteries (FIG. 7B).

Figure 8A:
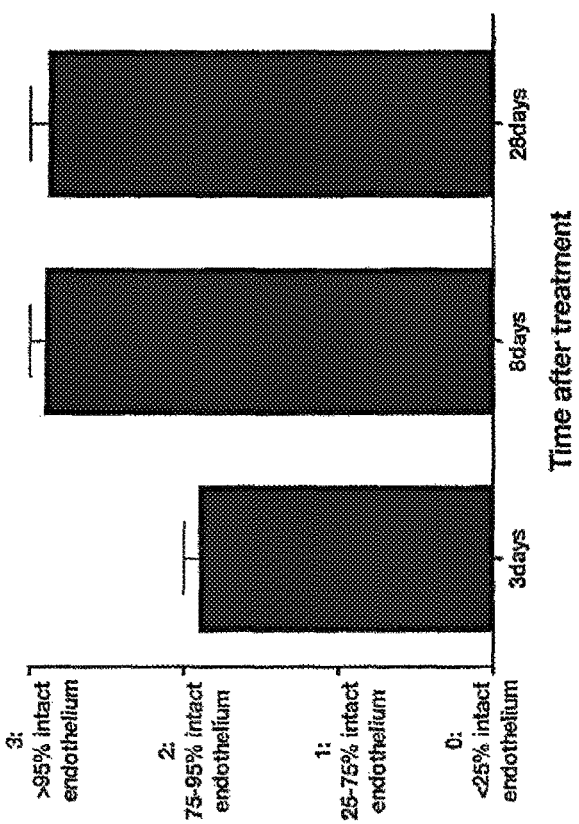
FIG. 8A shows the proliferative index after periadventitial delivery of Nab-rapamycin at days 3, 8, and 28.
Figure 8B:
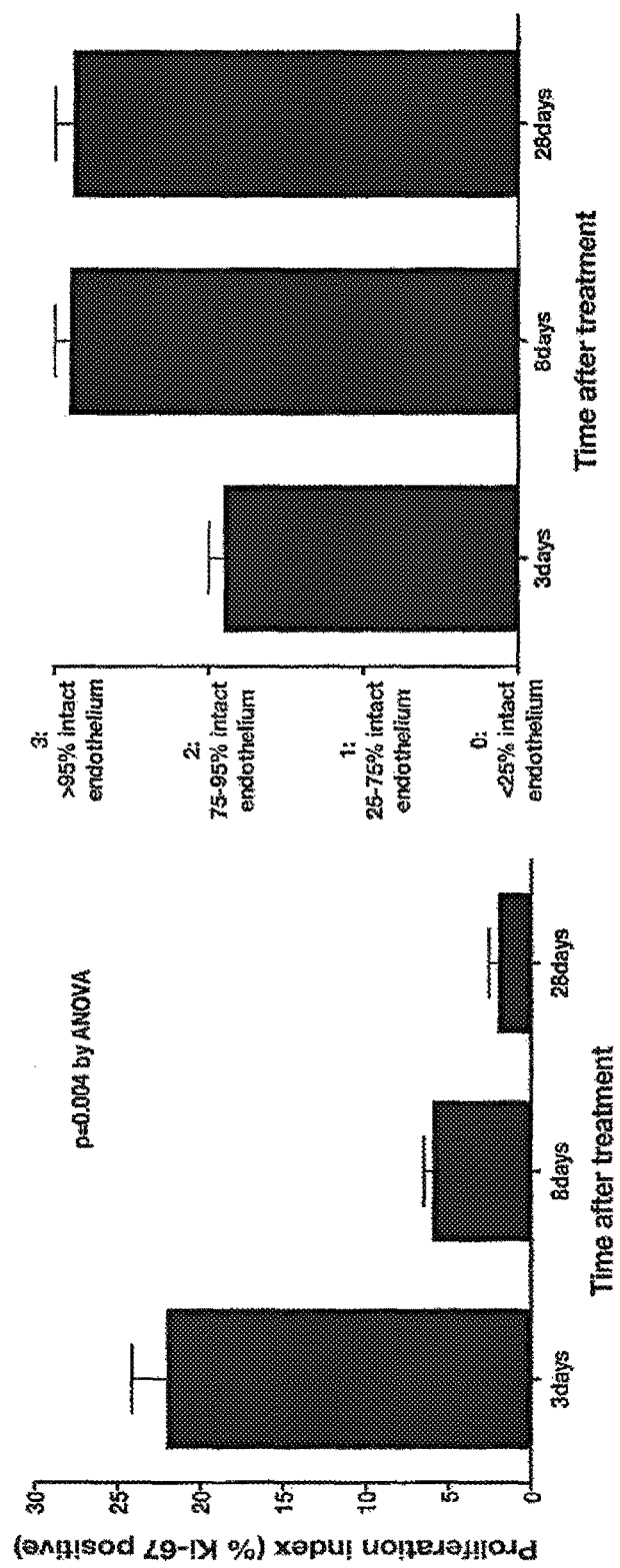
FIG. 8B shows the endothelialization after periadventitial delivery of Nab-rapamycin at days 3, 8, and 28.

Further pharmacokinetics analyses showed that the proliferation index fell significantly between 3 and 28 days in balloon-injured arteries treated with 500 µg Nab-rapamycin, p=0.004 (ANOVA)(FIG. 8A). Re-endotheolialization occurred by 8 days (FIG. 8B).

Figure 9B:
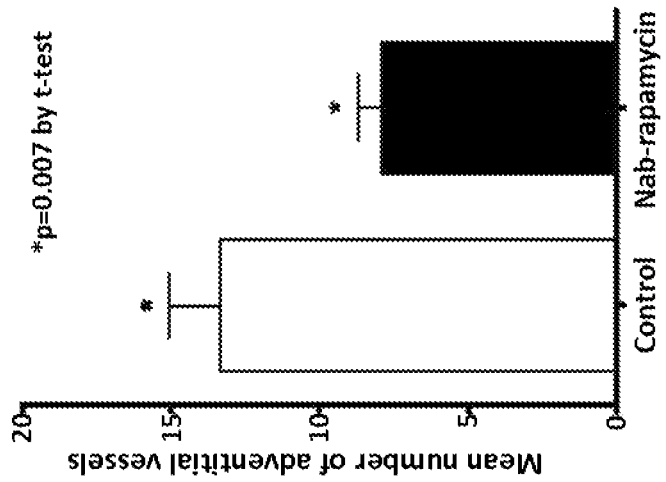
FIG. 9B shows mean number of adventitial vessels after periadventitial delivery of Nab-rapamycin or a control at day 28.
Figure 9A:
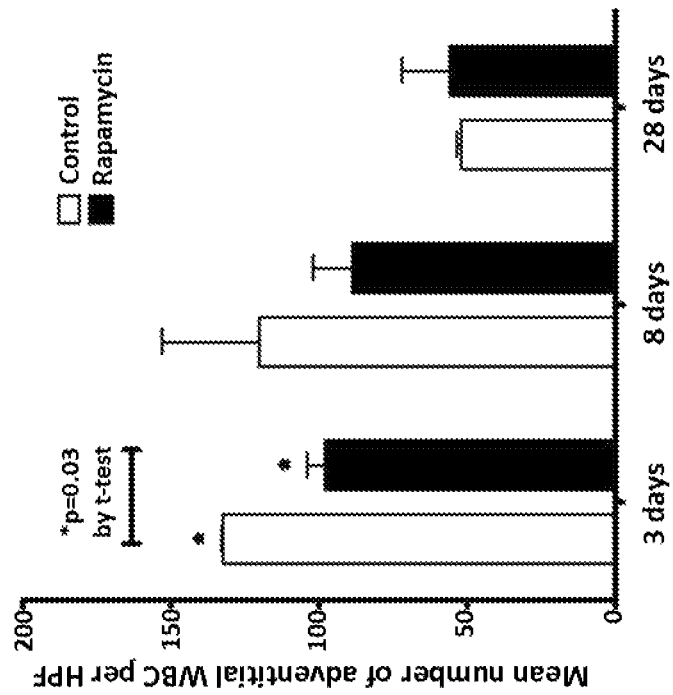
FIG. 9A shows adventitial leukocyte infiltration after periadventitial delivery of Nab-rapamycin or a control at days 3, 8, and 28.

Additionally, at 3 days, there were significantly fewer adventitial leukocytes in arteries treated with periadventitial Nab-rapamycin (FIG. 9A). By 28 days, Nab-rapamycin treated arteries had significantly fewer adventitial vessels (FIG. 9B).

The results reported herein demonstrate that periadventitial delivery of Nab-rapamycin is associated with a transient increase and rapid fall in serum rapamycin levels. At 1 hour after treatment, rapamycin levels in the perivascular tissue were over 1500 times those in the blood and rapamycin was retained in the perivascular tissue for at least 8 days (FIG. 5B). Balloon injured femoral arteries treated with Nab-rapamycin were significantly larger than vehicle treated arteries, suggesting less negative remodeling. Furthermore, periadventitial delivery of Nab-rapamycin leads to significant decrease in medial fibrosis.

Nab-rapamycin treated arteries demonstrated significantly less early (3 day) adventitial leukocyte infiltration. The Ki-67 proliferation index of Nab-rapamycin treated arteries was significantly lower at 28 days (FIG. 8A).

Figure 10:
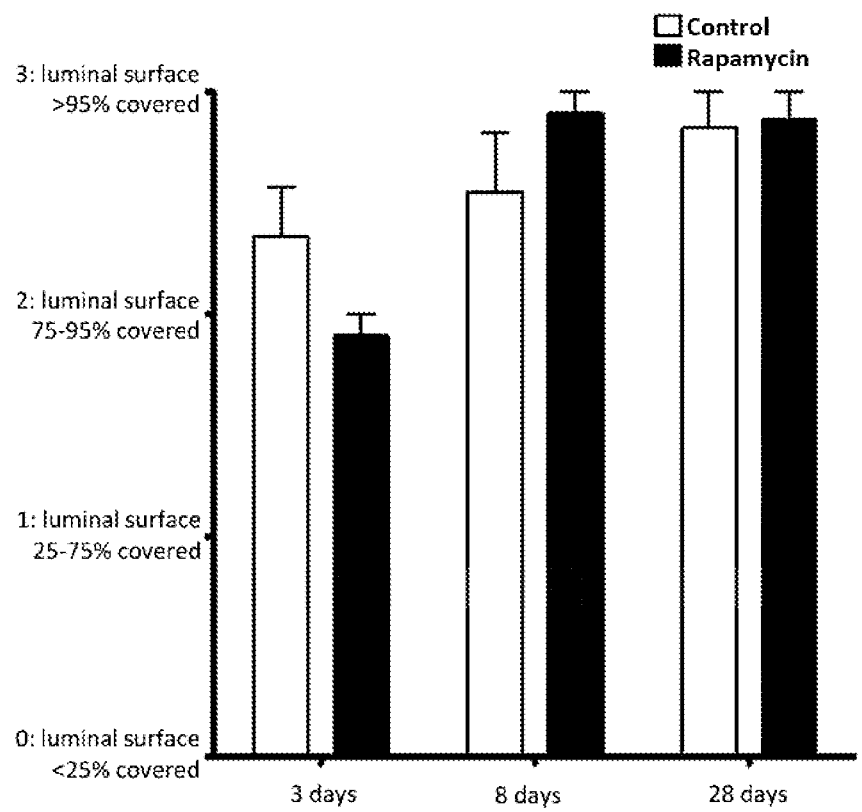
FIG. 10 shows re-endothelialization of target arteries after periadventitial delivery of Nab-rapamycin or a control at days 3, 8, and 28.

There was no difference in endothelialization at 28 days in control and Nab-rapamycin treated femoral arteries, and re-endothelialization to balloon-injured Nab-rapamycin treated vessels appeared to occur in the first week and appeared to complete by 8 days (FIG. 10). Nab-rapamycin treatment leads to a significantly lower proliferation and significantly lower medial fibrosis scores, suggesting a mechanism by which rapamycin may affect remodeling in balloon-injured femoral arteries.

A decrease in early adventitial leukocyte infiltration and subsequent reduction in medial fibrosis and Ki-67 proliferation index at 28 days suggests a mechanism by which periadventitial Nab-rapamycin may have an effect.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of inhibiting negative remodeling in a blood vessel in an individual in need thereof, comprising injecting into the blood vessel wall or tissue surrounding the blood vessel wall an effective amount of a composition comprising nanoparticles comprising rapamycin and an albumin.

2. A method of delivering a composition comprising nanoparticles comprising albumin and rapamycin to a blood vessel in an individual, wherein the method comprises injecting into the blood vessel wall or tissue surrounding the blood vessel wall an effective amount of a composition comprising nanoparticles comprising rapamycin and an albumin.

3. The method of claim 2, wherein the blood vessel is an artery.

4. The method of claim 2, wherein the blood vessel is a vein.

5. The method of claim 2, wherein the nanoparticle composition is injected into the blood vessel wall.

6. The method of claim 2, wherein the nanoparticle composition is injected into the tissue surrounding the blood vessel wall.

7. The method of claim 2, wherein the nanoparticle composition is injected at a dose of about 0.001 mg to about 100 mg.

8. The method of claim 2, wherein the injection volume of the nanoparticle composition is about 0.01 ml to about 50 ml.

9. The method of claim 2, wherein the nanoparticle composition is injected though a catheter with a needle.

10. The method of claim 2, wherein the nanoparticle composition is injected at least once a year.

11. The method of claim 2, wherein the nanoparticle composition is injected distal or proximal to the disease site.

12. The method of claim 2, wherein the nanoparticle composition is injected at least about 2 cm away from the disease site.

13. The method of claim 2, wherein the nanoparticle composition is injected at or adjacent to the disease site.

14. The method of claim 2, wherein the individual has any one of: angina, myocardial infarction, congestive heart failure, cardiac arrhythmia, peripheral artery disease, claudication, or chronic limb ischemia.

15. A catheter with a needle, wherein the needle contains a composition comprising nanoparticles comprising rapamycin and an albumin.

16. The method of claim 1, wherein the blood vessel is an artery.

17. The method of claim 16, wherein the artery is a coronary artery or a peripheral artery.

18. The method of claim 1, wherein the nanoparticle composition is injected into the blood vessel wall.

19. The method of claim 1, wherein the nanoparticle composition is injected into the tissue surrounding the blood vessel wall.

20. The method of claim 19, wherein the nanoparticle composition is injected into the adventitial tissue of the blood vessel.

21. The method of claim 1, wherein the nanoparticle composition is injected though a catheter with a needle.

* * * * *